(12) United States Patent
Seip et al.

(10) Patent No.: US 10,695,078 B2
(45) Date of Patent: Jun. 30, 2020

(54) INFUSION SYSTEM AND METHOD FOR SONOTHROMBOLYSIS STROKE TREATMENT

(71) Applicant: KONINKLIJKE PHILIPS N.V., Eindhoven (NL)

(72) Inventors: Ralf Seip, Carmel, NY (US); Evgeniy Leyvi, Arlington, MA (US); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 103 days.

(21) Appl. No.: 15/735,981

(22) PCT Filed: Jun. 23, 2016

(86) PCT No.: PCT/IB2016/053731
§ 371 (c)(1),
(2) Date: Dec. 13, 2017

(87) PCT Pub. No.: WO2017/001980
PCT Pub. Date: Jan. 5, 2017

(65) Prior Publication Data
US 2018/0185040 A1  Jul. 5, 2018

Related U.S. Application Data

(60) Provisional application No. 62/186,606, filed on Jun. 30, 2015.

(51) Int. Cl.
*A61M 5/142* (2006.01)
*B01F 13/08* (2006.01)
(Continued)

(52) U.S. Cl.
CPC .......... *A61B 17/22* (2013.01); *A61M 5/1456* (2013.01); *A61N 7/00* (2013.01); *B01F 13/0023* (2013.01); *B01F 13/0818* (2013.01); *A61B 2017/22088* (2013.01); *A61B 2017/22089* (2013.01); *A61M 5/1415* (2013.01); *A61M 2210/0693* (2013.01);
(Continued)

(58) Field of Classification Search
CPC .............. B01F 13/0818; B01F 13/0827; B01F 2215/0034; A61N 2007/0039
See application file for complete search history.

(56) References Cited

U.S. PATENT DOCUMENTS

| 4,741,732 A * | 5/1988 | Crankshaw ......... A61M 5/1723 604/155 |
| 6,706,020 B1 | 3/2004 | Urich |

(Continued)

*Primary Examiner* — Manuel A Mendez
*Assistant Examiner* — Courtney B Frederickson

(57) ABSTRACT

An infusion system for sonothrombolysis treatment uses a syringe loaded with a microbubble solution and operated by a syringe pump to deliver the microbubble solution to a subject during sonothrombolysis treatment. To prevent the stratification of the microbubble solution in the barrel of the syringe during treatment, the barrel also contains a plurality of magnetic beads which are agitated into semi-random patterns of motion in the syringe chamber during the procedure. The magnetic beads are moved by magnetic attraction and repulsion from the moving magnets of a magnetic stirrer mounted in proximity to the syringe during treatment.

19 Claims, 3 Drawing Sheets

(51) Int. Cl.
*A61B 17/22* (2006.01)
*A61M 5/145* (2006.01)
*B01F 13/00* (2006.01)
*A61N 7/00* (2006.01)
*A61M 5/14* (2006.01)

(52) U.S. Cl.
CPC .. *A61M 2210/12* (2013.01); *A61N 2007/0021* (2013.01); *A61N 2007/0039* (2013.01); *B01F 2215/0034* (2013.01)

(56) References Cited

U.S. PATENT DOCUMENTS

| | | | |
|---|---|---|---|
| 6,726,650 B2 * | 4/2004 | Schneider | A61M 5/007 |
| | | | 604/82 |
| 6,783,003 B2 * | 8/2004 | Simm | A61M 5/008 |
| | | | 206/366 |
| 10,159,948 B2 * | 12/2018 | Seaward | B01F 11/0054 |
| 2002/0154570 A1 | 10/2002 | Gebrian | |
| 2003/0126914 A1 | 7/2003 | Hvidtfeldt et al. | |
| 2004/0253183 A1 * | 12/2004 | Uber, III | A61K 49/223 |
| | | | 424/9.52 |
| 2009/0012497 A1 | 1/2009 | Uber, III et al. | |
| 2015/0131405 A1 * | 5/2015 | Zhou | B01F 5/0647 |
| | | | 366/144 |

\* cited by examiner

INFUSION SYSTEM AND METHOD FOR SONOTHROMBOLYSIS STROKE TREATMENT

This application is the U.S. National Phase application under 35 U.S.C. § 371 of International Application No. PCT/IB2016/053731, filed on Jun. 23, 2016, which claims the benefit of U.S. Provisional Application Ser. No. 62/186,606, filed Jun. 30, 2015. These applications are hereby incorporated by reference herein.

This invention relates to medical diagnostic ultrasound systems and, in particular, to ultrasound systems and methods for sonothrombolysis stroke therapy.

Ischemic stroke is one of the most debilitating disorders known to medicine. The blockage of the flow of blood to the brain can rapidly result in paralysis or death. Attempts to achieve recanalization through thrombolytic drug therapy such as treatment with tissue plasminogen activator (t-PA) has been reported to cause symptomatic intracerebral hemorrhage in a number of cases. Advances in the diagnosis and treatment of this crippling affliction are the subject of continuing medical research.

Sonothrombolysis is an emerging treatment modality for stroke that uses ultrasound targeting of the site of the occluding clot, microbubbles in systemic circulation, and sometimes t-PA, to break up the fibrin structures that make up a typical clot, so as to try to restore normal blood flow to the occluded region in the brain. As used in this application, microbubbles are sometimes referred to as "vascular acoustic resonators," or VARs. Such treatments typically use head-mounted, single-element transducer(s) or array transducers to deliver the ultrasound through the temporal bone, and operate in continuous or pulsed mode. International patent publication WO 2008/017997 (Browning et al.) describes a sonothrombolysis ultrasound system which provides microbubble-mediated therapy to a clot causing ischemic stroke. Microbubbles are infused, delivered in a bolus injection, or developed in the bloodstream and flow to the vicinity of a thrombus. Ultrasound energy is delivered to microbubbles at the site of the clot to disrupt or rupture the microbubbles. This microbubble activity can in many instances aid in dissolving or breaking up the blood clot and return a nourishing flow of blood to the brain and other organs. Such microbubble activity can be used to deliver drugs encapsulated in microbubble shells, and well as microbubble-mediated sonothrombolysis.

Clinical trials are ongoing in sonothrombolysis, using either a combination of ultrasound and t-PA, ultrasound and microbubbles, and/or ultrasound, t-PA, and microbubbles combined. In these trials a continuous flow of microbubbles is infused into the subject's blood stream from a syringe pump while ultrasound is delivered for upwards of an hour to assure that blood clots are completely lysed. This treatment regimen constantly replenishes the flow of microbubbles to the therapy site and thus requires a continuous infusion of a constant amount of microbubbles during the treatment period. A problem that has arisen during such lengthy periods of infusion is that the buoyancy of the microbubbles causes them to migrate to the top of the fluid in the syringe and stratify in levels of different microbubble concentration. This leads to different concentrations being infused into the body over time, which is not desirable, as it introduces treatment uncertainties.

A system which has been developed to address microbubble stratification is illustrated in FIG. 1. This illustration shows an ultrasound system which is delivering ultrasound to the brain of a patient through a headset 12 containing ultrasound transducers. A saline bag 14 would normally deliver a flow of fluid containing microbubbles to the vascular system of the patient through the tubing of an infusion set. Instead, the microbubble fluid is delivered from a syringe 16 which is operated by a specially modified syringe pump 18. The pump 18 includes a mechanism which gently rocks/rotates the syringe during the procedure, which alleviates the tendency of the microbubbles to stratify in the syringe. This is an ideal solution to prevent stratification during ultrasonic contrast imaging where the problem of microbubble migration in the syringe is not excessive, as these procedures tend to be short, often rely on a microbubble bolus injection, and in-situ microbubble concentration is not critical. However, experiments with this arrangement has shown that when infusion continues in excess of ten minutes, microbubbles still tend to settle at the top of the syringe, indicating that the rocking/rotation motion is not sufficient to counteract microbubble buoyancy over extended periods of time. While this system potentially alleviates microbubble migration due to buoyancy for ultrasound contrast imaging applications, it does not solve the problem for constant microbubble concentration delivery over a longer period of time required for sonothrombolysis.

In accordance with the principles of the present invention, a sonothrombolysis infusion system and method deliver a constant supply of microbubbles from a syringe containing a microbubble solution and magnetic stirrer beads. Located in proximity to the syringe is a motorized magnetic stirrer. As the magnets of the stirrer move past the syringe they cause the magnetic beads to move in random or semi-random patterns of motion, continuously agitating the microbubble solution in the syringe and preventing microbubble stratification. In a preferred implementation the magnetic stirrer has a rotating rod with magnets on it, which can be mounted with the syringe by a retention mechanism of a syringe pump. The rotational speed of the magnetic stirrer can be varied so that its speed is sufficient to prevent microbubble stratification while maintaining the structural integrity of the microbubbles.

Figure 1:
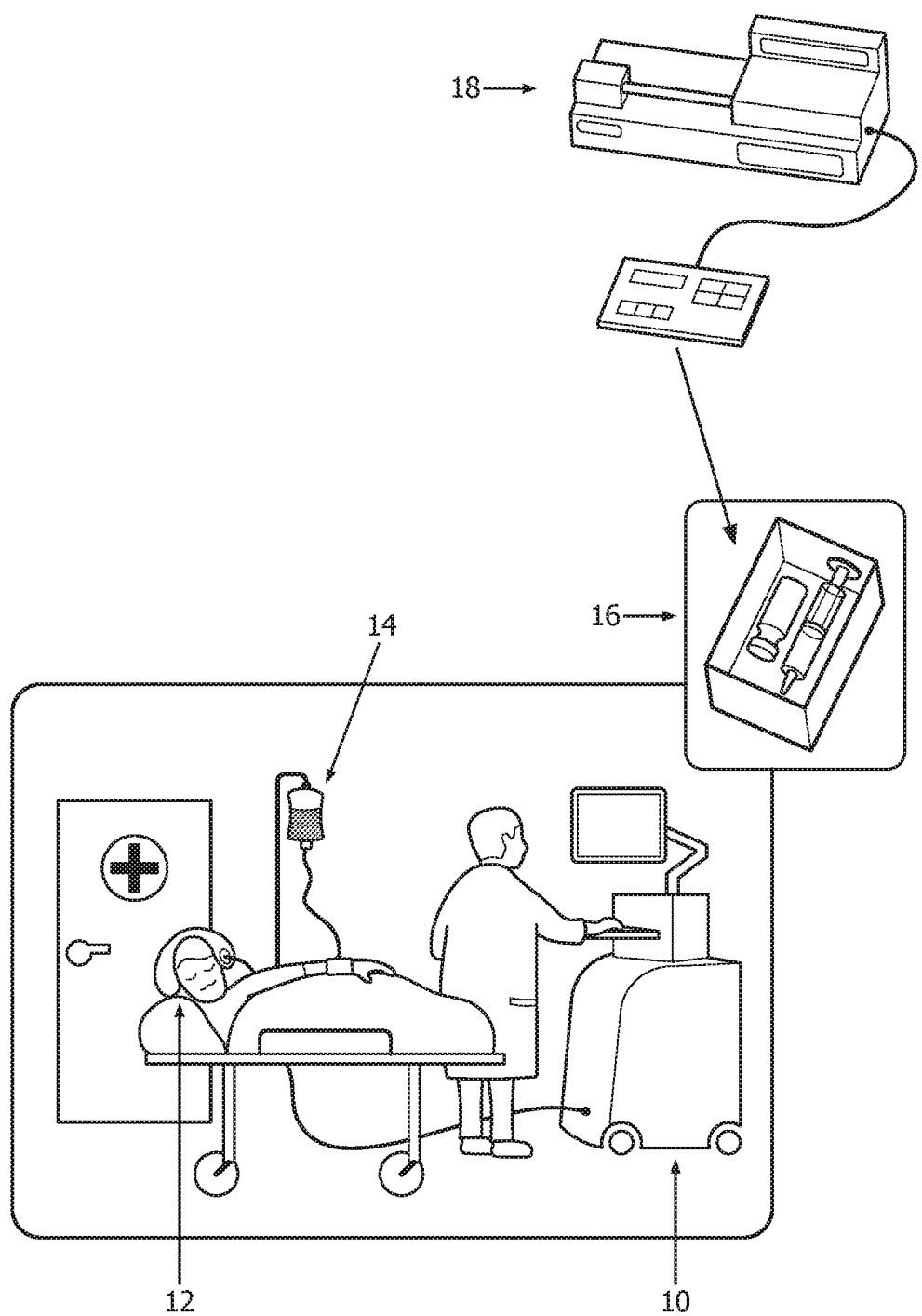
FIG. 1 illustrates the setup of a sonothrombolysis procedure including the delivery of infusing microbubbles with a syringe pump.
Figure 2:
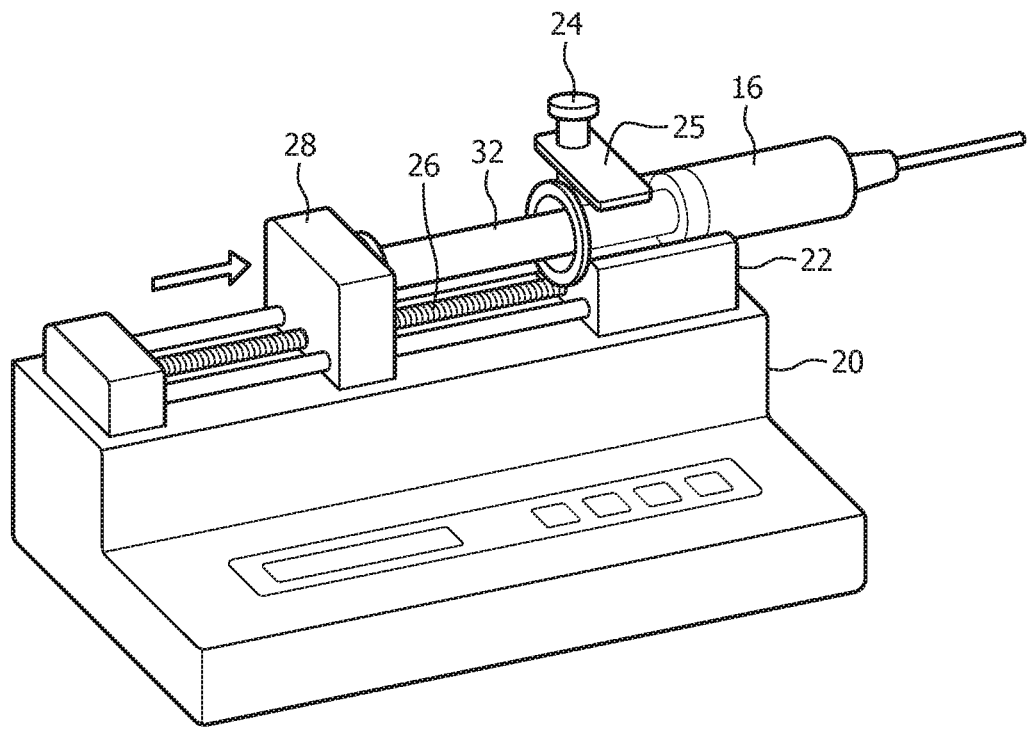
FIG. 2 is a perspective view of a standard syringe pump.

Referring to FIG. 2, a conventional syringe pump is shown in a perspective view. The lower housing 20 contains a variable speed motor with gear train and a processor which controls the speed at which the motor rotates a worm gear 26 that advances a plate 28 mounted on two guide rods. The plate 28 advances as indicated by the arrow, pressing the plunger 32 of a syringe 16 into the barrel of the syringe (indicated at 16) and thereby expelling the fluid in the syringe at a controlled rate of flow. The barrel of the syringe rests in a groove in a syringe mount 22 during operation and is retained in place by a spring-loaded bar 25 that is positioned onto the syringe barrel by a release knob 24. With the syringe barrel held in place by the bar 25, the plate 28 advances to the right, pressing the plunger 32 into the syringe and expelling its fluid out the distal end of the syringe.

Figure 3:
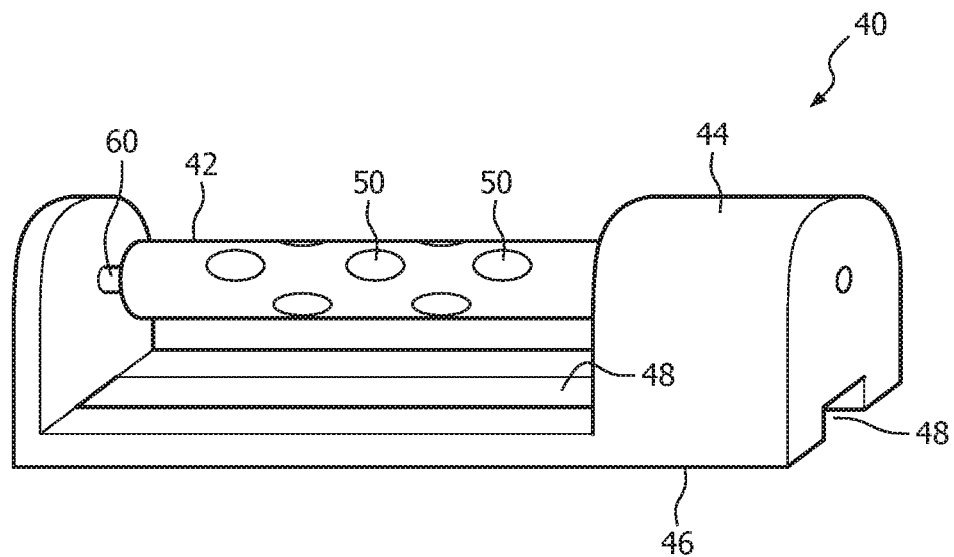
FIG. 3 illustrates a microbubble stirrer device constructed in accordance with the principles of the present invention.

FIG. 3 illustrates in perspective a magnetic stirrer 40 constructed in accordance with the principles of the present invention. The stirrer comprises a frame with an enclosure 44 at one end which houses a motor and its reduction gearbox. In a constructed embodiment the motor is a 6 volt motor with a drive shaft speed variable up to 200 rpm. The motor rotates an aluminum rod 42 having a bearing-mounted shaft 60. In a constructed embodiment the rod is about 5 cm in length, which is sufficient to oppose the barrel of a 30 cc syringe. Affixed around the outer circumference of the rod 42 are a number of disc magnets 50. A groove 48 is formed in the base 46 of the stirrer 40 and extends along the entire length of the frame.

Figure 4:
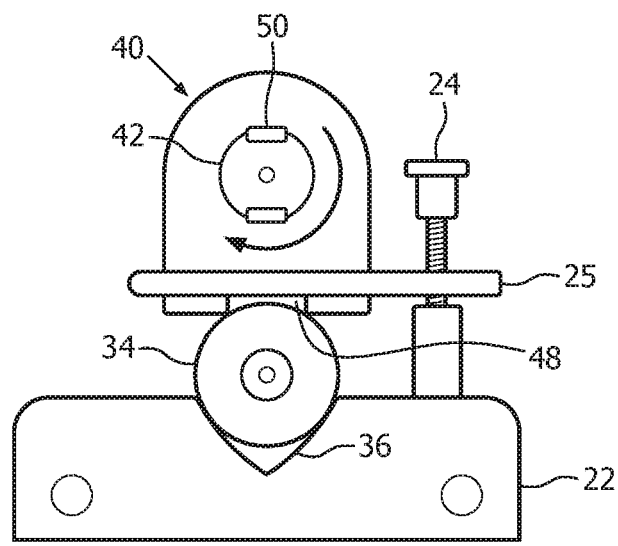
FIG. 4 is a partially cross-sectional end view of the stirrer device of FIG. 3 when mounted in proximity to a syringe by a syringe pump.

The stirrer 40 is shown in use in a partially cross-sectional end view in FIG. 4 when mounted on the barrel 34 of a syringe in a syringe pump. The barrel 34 of the syringe is seen to rest in a groove 36 in the syringe mount 22 of the syringe pump, and would normally be held in place by the spring-loaded bar 25. But in this implementation of the invention the stirrer 40 is positioned on top of the syringe barrel with the barrel extending partially into the groove 48 in the base 46 of the stirrer. The spring-loaded bar 25 extends through the stirrer, retaining stirrer base 46 in position on top of the syringe and the syringe in its proper position in the syringe pump. The rotating rod 42 and its magnets 50 are thus maintained in a substantially parallel alignment with the barrel of the syringe. When the stirrer is actuated, its motor rotates the rod 42 as indicated by the curved arrow, and the magnets 50 on the circumference of the rod 42 are continually rotated over the syringe, moving the magnetic beads inside the syringe barrel 34 through magnetic attraction and repulsion. While the groove 48 in this implementation is seen to be a squared groove, the groove can also be a concave curved groove which contacts more of the surface of the syringe barrel when engaged. However a squared groove 48 as shown has been found to be sufficient to engage the syringe and be held in place by the bar 25.

Figure 5:
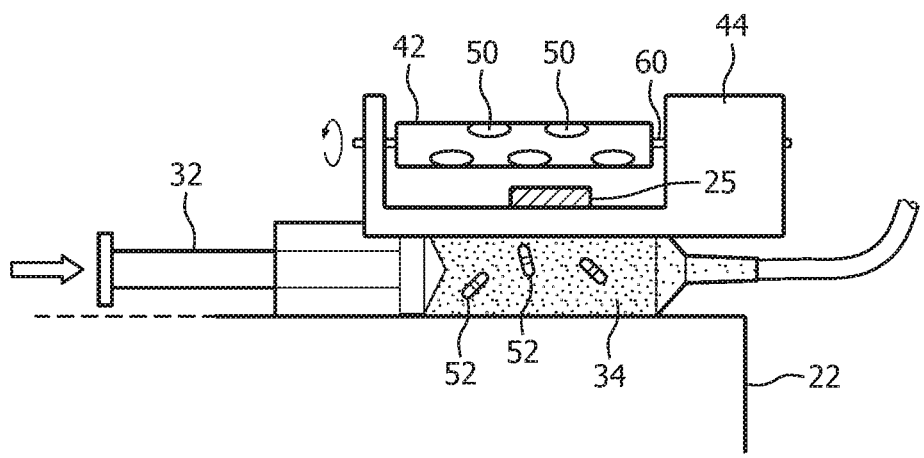
FIG. 5 is a side view of the stirrer device of FIG. 3 mounted in proximity to a syringe by a syringe pump.

FIG. 5 is a side view of the assembly of FIG. 4. This illustration shows the magnetic beads 52 in the microbubble solution in the syringe barrel 34. As the rod 42 rotates as indicated by the arrow, the passage of the magnets 50 in close proximity to the syringe will cause the beads 52 to move in a semi-random pattern, agitating the microbubble solution and preventing stratification. In a constructed embodiment the magnets 50 are quarter-inch diameter (0.64 cm) Samarium cobalt disc magnets SC2512-500 available from Dura Magnetics, Inc. of Sylvania, Ohio, USA. The magnetic beads 52 are approximately 5 mm in length and 2 mm in diameter. Such beads are available from Cole-Parmer Instrument Company, LLC of Vernon Hills, Ill., USA as part number 08545-02. The magnets affixed to the stirrer rod 42 are powerful enough and pass close enough (approximately 5 mm) to the syringe barrel 34 and the magnetic beads 52 to move/spin the magnetic beads located inside the syringe. Thus, when the stirrer rod 42 is rotated by the stirrer motor, it rotates the magnets 50, which in turn move the magnetic beads 52 within the syringe, agitating the solution and thus preventing the microbubble solution from stratifying. At a rotation speed of 60-200 RPM, and preferably in the range of 60-100 RPM, this assembly easily stirs the microbubble solution without causing microbubble destruction. Other rotation speeds may be used, depending on factors such as the concentration of microbubbles, the number of beads used, and the size of the syringe. However, if the speed is too low, the microbubbles will still stratify; if the rotation speed is too high, the magnetic coupling between the magnets 50 on the stirrer rod 42 and the magnetic beads 52 separates, again resulting in insufficient stirring of the microbubble solution. Selective adjustment of the rotational speed is often required.

Since magnetic beads are generally not used to stir liquids to be infused into the body, the beads should be sterilized before being placed in the syringe. This may be done in the normal manner as by use of an autoclave, ethylene oxide gas, etc. Microbubble solutions are usually packaged in a vial with a rubber membrane as are other injectable liquids. The microbubble solution may be aspirated from such a vial by use of a 20 gauge or larger needle attached to the distal end of the syringe which pierces the membrane to withdraw the microbubble solution.

It is currently estimated that approximately 50 ml of microbubble solution is required for continuous infusion during a one hour sonothrombolysis treatment. This equates to a flow rate of 0.83 ml/min. This means that the amount of microbubble solution in the syringe should be 50 ml plus an additional amount to enable priming of the infusion tube set, plus a further amount to account for the inability to fully depress the plunger to the end of the syringe barrel due to the presence of the magnetic beads in the barrel of the syringe. Experience has shown that this additional amount of microbubble solution is about 10 ml, bringing the total amount of solution required to about 60 ml in many cases.

As microbubble stratification can occur to at least some degree in the tubing set after the microbubble solution has been aspirated from the syringe, it is desirable to keep the length of the tubing as short as possible between the distal end of the syringe and the catheterized infusion site. Preferably the tubing length is restricted to 30 cm or less. Tubing length of 10 cm or less has been found to result in no significant microbubble stratification in the infusion tubing. A significant rate of flow will also help prevent stratification.

In use, several sterile magnetic beads, at least two or more, are placed in the barrel of a syringe and the plunger inserted as far as it can go into the barrel. A 12 gauge or larger needle is attached to the distal end of the syringe and used to pierce the membrane of a vial of microbubble solution. The solution is drawn into syringe by retracting the plunger until the required amount of solution, generally 50 ml or more, fills the syringe. The syringe needle is pointed upward and the plunger depressed slightly to expel any air in the barrel. The needle is removed and infusion tubing leading to a transcutaneous catheter is attached to the distal end of the syringe. The syringe is placed in the groove of the syringe mount of a syringe pump and the magnetic stirrer placed on the barrel of the syringe. The spring-loaded retention bar of the syringe pump is inserted through the stirrer and springs downward to hold the stirrer and syringe in place on the pump and the stirrer is turned on. If necessary, its speed is adjusted so that stratification is prevented without significant microbubble destruction. The syringe pump is actuated to prime the tubing, if necessary, by injecting microbubble solution (or saline) into the tubing. After priming the catheter is inserted into a vein of the patient. The syringe pump is actuated to begin the injection of a continuous, controlled amount of microbubble solution into the patient while ultrasound is administered to the patient transcranially. An injection of t-PA can be added to the solution if desired via another infusion pump and connected tubing. At the conclusion of the ultrasonic treatment the syringe pump is stopped, the stirrer turned off, and the catheter withdrawn from the vein of the patient.

What is claimed is:

1. A sonothrombolysis infusion system comprising:
a syringe pump;

a syringe having a barrel, which in operation holds a microbubble solution and a plurality of magnetic beads added thereto, the syringe being mounted on the syringe pump; and a magnetic stirrer coupled to the syringe pump such that the magnetic stirrer is in proximity to the barrel of the syringe while the syringe is actuated by the syringe pump for dispensing the microbubble solution, wherein the magnetic stirrer comprises a rotatable rod having a plurality of magnets thereon, wherein the magnets are arranged on the rotatable rod to magnetically interact with the plurality of magnetic beads in the barrel to cause the plurality of magnetic beads to stir the microbubble solution in the syringe responsive to rotation of the rotatable rod while the microbubble solution is being dispensed from the syringe, wherein the syringe pump further comprises a retention bar for retaining the syringe in a mounted position on the syringe pump, and wherein the magnetic stirrer is configured to receive the retention bar for coupling the magnetic stirrer to the syringe pump and holding the magnetic stirrer in proximity to barrel of the syringe during dispensing of the microbubble solution from the syringe.

2. The sonothrombolysis infusion system of claim 1, wherein the magnetic stirrer is placed on the syringe for coupling the magnetic stirrer to the syringe pump.

3. The sonothrombolysis infusion system of claim 2, wherein the rotatable rod is substantially parallel to the barrel of the syringe when the magnetic stirrer is placed on the syringe.

4. The sonothrombolysis infusion system of claim 2, wherein the magnetic stirrer further comprises a motor, coupled to the rotatable rod, to rotate the rod at a selectable speed of rotation.

5. The sonothrombolysis infusion system of claim 4, wherein the selectable speed of rotation is within the range of 60-200 RPM.

6. The sonothrombolysis infusion system of claim 4, wherein the selectable speed of rotation is less than 100 RPM.

7. The sonothrombolysis infusion system of claim 6, wherein each of the plurality of magnetic beads has a dimension of at least 2 mm.

8. The sonothrombolysis infusion system of claim 7, wherein each of the plurality of beads is about 5 mm in length.

9. The sonothrombolysis infusion system of claim 4, wherein the motor is housed in an enclosure of a frame of the magnetic stirrer, the frame comprising a groove configured to receive the barrel of the syringe at least partially therein.

10. The sonothrombolysis infusion system of claim 9, wherein the frame is configured to allow the retention bar of the syringe pump to pass through the magnetic stirrer for mounting the magnetic stirrer to the syringe pump.

11. The sonothrombolysis infusion system of claim 10, wherein the retention bar is positioned between the rotatable bar and the barrel when the magnetic stirrer and syringe are mounted to the syringe pump by the retention bar.

12. The sonothrombolysis infusion system of claim 1, wherein the retention bar comprises a spring-loaded retention bar; and wherein the syringe pump further comprises a release knob coupled to the spring-loaded retention bar.

13. The sonothrombolysis infusion system of claim 1, wherein the magnets are arranged on the rotatable rod to cause the magnetic beads in the barrel to move in a random motion within the barrel.

14. A method for delivering a microbubble solution to a subject for sonothrombolysis treatment, the method comprising:

providing a sonothrombolysis infusion system according to claim 1;

placing a plurality of magnetic beads in the barrel of the syringe;

at least partially filling the barrel of the syringe containing the plurality of magnetic beads with a microbubble solution;

mounting the syringe on the syringe pump;

connecting an infusion tube to the syringe;

coupling the magnetic stirrer to the syringe pump such that the magnetic stirrer is in proximity to the barrel of the syringe, wherein the magnetic stirrer comprises the rotatable rod having the plurality of magnets thereon; and actuating the syringe pump to cause the microbubble solution to be dispensed from the syringe while rotating the rotatable rod to cause the magnets to magnetically interact with the plurality of magnetic beads in the barrel for stirring the microbubble solution during dispensing of the microbubble solution from the syringe.

15. The method of claim 14, wherein filling the barrel of the syringe with a microbubble solution further comprises:

drawing the microbubble solution into the barrel of the syringe through a syringe needle of size 20 gauge or larger; and removing the needle from the syringe prior to connecting the infusion tube to the syringe.

16. The method of claim 14, wherein coupling the magnetic stirrer to the syringe pump comprises placing the magnetic stirrer on the syringe and retaining the magnetic stirrer on the syringe with the syringe pump retention bar.

17. The method of claim 14, wherein coupling the magnetic stirrer to the syringe pump such that the magnetic stirrer is in proximity to the barrel of the syringe further comprises positioning the magnetic stirrer with the rotatable rod substantially parallel to the barrel of the syringe.

18. The method of claim 14, wherein the magnetic stirrer further comprises a motor coupled to the rotatable rod to rotate the rod at a speed of rotation selected to prevent microbubble stratification in the barrel of the syringe without causing destruction of the microbubbles.

19. The method of claim 14, further comprising priming the infusion tube with microbubble solution.

* * * * *